United States Patent
Kaur

(10) Patent No.: US 10,799,179 B2
(45) Date of Patent: Oct. 13, 2020

(54) GENERATING SPECIFICATIONS FOR AN ORTHOSIS

(71) Applicant: ENT. SERVICES DEVELOPMENT CORPORATION LP, Houston, TX (US)

(72) Inventor: Satwant Kaur, Mt. View, CA (US)

(73) Assignee: ENT. SERVICES DEVELOPMENT CORPORATION LP, Houston, TX (US)

( * ) Notice: Subject to any disclaimer, the term of this patent is extended or adjusted under 35 U.S.C. 154(b) by 375 days.

(21) Appl. No.: 15/305,258

(22) PCT Filed: Jun. 26, 2014

(86) PCT No.: PCT/US2014/044337
§ 371 (c)(1),
(2) Date: Oct. 19, 2016

(87) PCT Pub. No.: WO2015/199699
PCT Pub. Date: Dec. 30, 2015

(65) Prior Publication Data
US 2017/0173885 A1   Jun. 22, 2017

(51) Int. Cl.
*G01L 7/00* (2006.01)
*A61B 5/00* (2006.01)
*A43B 17/00* (2006.01)
*A61F 5/01* (2006.01)
*A43D 1/02* (2006.01)
(Continued)

(52) U.S. Cl.
CPC .......... *A61B 5/6829* (2013.01); *A43B 3/0005* (2013.01); *A43B 17/00* (2013.01); *A43D 1/02* (2013.01); *A61B 5/1038* (2013.01); *A61F 5/01* (2013.01); *B29C 64/112* (2017.08); *B29C 64/20* (2017.08); *B29C 64/386* (2017.08); *B33Y 10/00* (2014.12); *B33Y 30/00* (2014.12); *B33Y 50/02* (2014.12)

(58) Field of Classification Search
None
See application file for complete search history.

(56) References Cited

U.S. PATENT DOCUMENTS

| 6,183,425 B1 | 2/2001 | Whalen et al. |
| 6,505,522 B1 | 1/2003 | Wilssens |
(Continued)

FOREIGN PATENT DOCUMENTS

| BR | PI1103691 | 7/2013 |
| WO | WO-2012055029 | 5/2012 |

OTHER PUBLICATIONS

Crea, S. et al.; "A Wireless Flexible Sensorized Insole for Gait Analysis"; Jan. 9, 2014; 17 pages, Download date Oct. 19, 2016. http://www.mdpi.com/1424-8220/14/1/1073/htm.
(Continued)

*Primary Examiner* — Aditya S Bhat
(74) *Attorney, Agent, or Firm* — Sheppard Mullin Richter & Hampton LLP

(57) ABSTRACT

Example implementations relate to collecting data to generate specifications for an orthosis. In example implementations, data may be collected from a plurality of pressure sensors. Histograms may be generated that characterize collected data. Specifications for an orthosis may be generated based on the histograms.

20 Claims, 6 Drawing Sheets

(51) Int. Cl.
*B29C 64/386* (2017.01)
*B29C 64/112* (2017.01)
*B29C 64/20* (2017.01)
*B33Y 10/00* (2015.01)
*B33Y 30/00* (2015.01)
*B33Y 50/02* (2015.01)
*A43B 3/00* (2006.01)
*A61B 5/103* (2006.01)

(56) References Cited

U.S. PATENT DOCUMENTS

| | | | |
|---|---|---|---|
| 7,493,230 B2 | 2/2009 | Schwartz et al. | |
| 10,060,810 B2* | 8/2018 | Lee | G01L 1/02 |
| 10,149,637 B2* | 12/2018 | Latterman | A61B 5/1072 |
| 10,463,257 B2* | 11/2019 | Schwartz | A61B 5/1077 |
| 2006/0070260 A1* | 4/2006 | Cavanagh | A43B 17/00 |
| | | | 36/44 |
| 2008/0109183 A1 | 5/2008 | Shoureshi et al. | |
| 2009/0076772 A1* | 3/2009 | Hinshaw | A43B 7/1465 |
| | | | 702/167 |
| 2011/0214501 A1* | 9/2011 | Ross | A43B 3/0005 |
| | | | 73/172 |
| 2013/0150755 A1* | 6/2013 | Kubiak | A61B 5/1036 |
| | | | 600/592 |
| 2013/0192071 A1 | 8/2013 | Esposito et al. | |
| 2015/0328840 A1* | 11/2015 | Zachariasen | A61F 5/01 |
| | | | 700/98 |

OTHER PUBLICATIONS

PCT Search Report/Written Opinion—Application No. PCT/US2014/044337 dated Feb. 25, 2015—12 pages.

Pfaffen, S. et al.; "Planipes: Mobile Foot Pressure Analysis"; Nov. 1, 2011; 6 pages http://www.tik.ee.ethz.ch/file/0006c5ad6987854ae039e5ad66772fa3/paper_243.pdf.

* cited by examiner

GENERATING SPECIFICATIONS FOR AN ORTHOSIS

CLAIM FOR PRIORITY

The present application is a national stage filing under 35 U.S.C. § 371 of PCT application number PCT/US2014/044337, having an international filing date of Jun. 26, 2014, the disclosure of which is hereby incorporated by reference in its entirety.

BACKGROUND

Orthotic devices may be used to support, brace, and/or improve functions of parts of the body. For example, people with flat feet may place insoles inside their shoes to provide arch support. Someone recovering from an ankle sprain/fracture may wear an ankle-foot orthosis to control position of the ankle and/or compensate for weakness in certain muscles. To better suit a person's individual needs, a custom orthosis may be made especially for the person.

BRIEF DESCRIPTION OF THE DRAWINGS

The following detailed description references the drawings, wherein.

DETAILED DESCRIPTION

Orthoses may be worn by people who experience muscle/joint weakness, nerve damage, or poor blood circulation. For example, diabetics who suffer from peripheral neuropathy may wear insoles in their shoes to provide extra support and cushioning, decreasing irritation by external objects. Custom insoles may be made that better conform to a person's feet. To make a custom insole, a person's foot may be dipped in plaster to form a mold/cast of the person's foot, and an insole may be formed based on the shape of the mold/cast. Some retailers or medical offices may scan a person's foot using a flatbed image scanner that shines light on the foot and determines the shape of the foot by measuring the intensity of light that is reflected back. Data from this scan may be used to create a custom insole.

Custom insoles created using the aforementioned methods may not be suitable for actual conditions in a person's daily life, as the person's cushioning/support needs may be different when the person is moving than when the person is standing still. In light of the above, the present disclosure provides for using a diagnostic insole having a plurality of pressure sensors to collect data as a person goes about his/her daily activities. Collecting data over a longer period of time (e.g., hours or days, as opposed to a few seconds in a store or doctor's office) may allow for the creation of a custom insole suited to actual conditions in a person's daily life.

Figure 1:
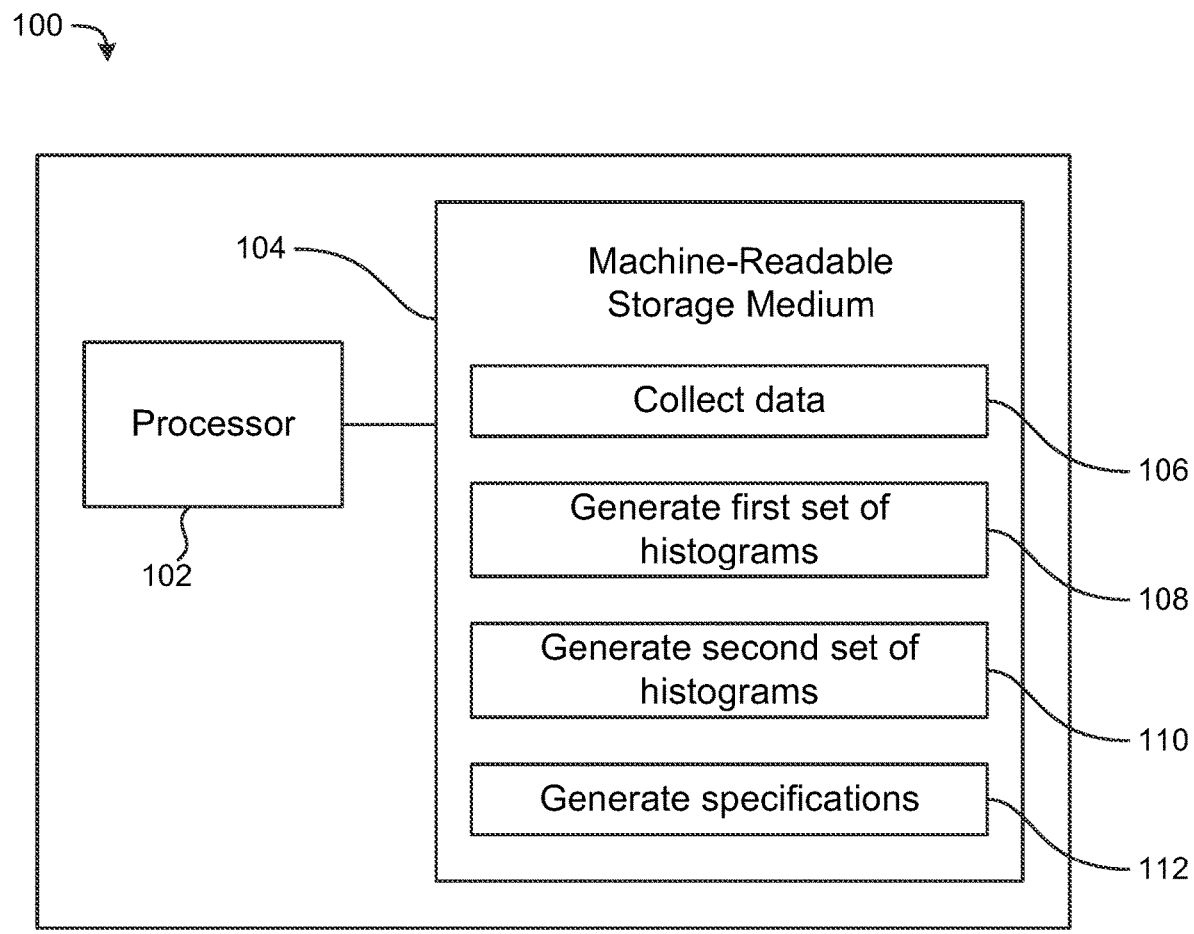
FIG. 1 is a block diagram of an example device that includes a machine-readable storage medium encoded with instructions to enable generating specifications for an orthosis.

Referring now to the drawings, FIG. 1 is a block diagram of an example device 100 that includes a machine-readable storage medium encoded with instructions to enable generating specifications for an orthosis. In some implementations, device 100 may be embedded in a diagnostic insole or other limb support structure (e.g., for a hand, shoulder, ankle, or knee). In some implementations, device 100 may be an electronic user device, such as a notebook computer, a desktop computer, a workstation, a tablet computing device, or a mobile phone. In FIG. 1, device 100 includes processor 102 and machine-readable storage medium 104. As used herein, the terms "include", "have", and "comprise" are interchangeable and should be understood to have the same meaning.

Processor 102 may include a central processing unit (CPU), microprocessor (e.g., semiconductor-based microprocessor), and/or other hardware device suitable for retrieval and/or execution of instructions stored in machine-readable storage medium 104. Processor 102 may fetch, decode, and/or execute instructions 106, 108, 110, and 112 to enable generating specifications for an orthosis, as described below. As an alternative or in addition to retrieving and/or executing instructions, processor 102 may include an electronic circuit comprising a number of electronic components for performing the functionality of instructions 106, 108, 110, and/or 112.

Machine-readable storage medium 104 may be any suitable electronic, magnetic, optical, or other physical storage device that contains or stores executable instructions. Thus, machine-readable storage medium 104 may include, for example, a RAM, an Electrically Erasable Programmable Read-Only Memory (EEPROM), a storage device, an optical disc, and the like. In some implementations, machine-readable storage medium 104 may include a non-transitory storage medium, where the term "non-transitory" does not encompass transitory propagating signals. As described in detail below, machine-readable storage medium 104 may be encoded with a set of executable instructions 106, 108, 110, and 112.

Instructions 106 may collect data from a plurality of pressure sensors. The plurality of pressure sensors may be in various locations on a diagnostic insole. For example, a diagnostic insole having the plurality of pressure sensors may be placed in a person's shoe, and data may be collected from the plurality of pressure sensors as the person goes about his/her daily routine. Data collected from the plurality of pressure sensors may include pressure values. Each pressure value may indicate an amount of pressure applied to one of the plurality of pressure sensors at a certain time. In some implementations, data may be collected from the plurality of pressure sensors over a plurality of days.

Although example implementations discussed herein refer to a diagnostic insole, it should be understood that the concepts discussed herein may be applicable to diagnostic support structures for other parts of the body (e.g., hand, shoulder, ankle, knee). Pressure sensors may be placed on a diagnostic insole/other support structure worn by a person as the person goes about his/her normal activities. Data collected by the pressure sensors may be used to create a custom insole or other customized support structure (orthosis) that suits the person's individual needs. Although example implementations discussed herein refer to orthoses worn by humans, it should be understood that the concepts discussed herein may be applicable to orthoses worn by animals.

Instructions 108 may generate a first set of histograms. A histogram may have a plurality of value ranges ("bins"), and each value range may include data values in the respective value range. Each histogram in the first set of histograms may correspond to a respective one of the plurality of pressure sensors, and may characterize a distribution of data collected from the respective one of the plurality of pressure sensors. For example, the plurality of pressure sensors may include a pressure sensor in the heel region of a diagnostic insole, and another pressure sensor in the big-toe region of the diagnostic insole. A histogram in the first set of histograms may correspond to the pressure sensor in the heel region, and may have a plurality of bins into which pressure values collected from the heel-region pressure sensor are sorted (e.g., a first bin may have pressure values between 0 and 1.5 pounds per square inch [psi], a second bin may have pressure values greater than 1.5 psi up to 3 psi, etc.). Another histogram in the first set of histograms may correspond to the pressure sensor in the big-toe region, and may have a plurality of bins into which pressure values collected from the big-toe-region pressure sensor are sorted.

The number of values in a bin of a histogram may be directly proportional to the amount of time the respective pressure sensor sensed an amount of pressure in the value range of the bin. For example, if a person tends to stand/walk/run on the balls of his/her feet, a histogram, in the first set of histograms generated from data collected from a diagnostic insole worn by the person, that corresponds to a pressure sensor in the big-toe region of the diagnostic insole may have a lot of data values in higher-value bins, while lower-value bins may not have as many data values. A histogram, in the first set of histograms, that corresponds to a pressure sensor in the heel region of the diagnostic insole may have a lot of data values in lower-value bins, while higher-value bins may not have as many data values.

Instructions 110 may generate a second set of histograms. Each histogram in the second set of histograms may correspond to a respective pair of the plurality of pressure sensors, and may characterize a distribution of averages of data collected from the respective pair of the plurality of pressure sensors. Pressure sensors in the plurality of pressure sensors may be paired based on physical proximity; for example, a pressure sensor in the big-toe region of a diagnostic insole may be paired with a pressure sensor in the ball-of-the-foot region of the diagnostic insole, and two pressure sensors in the heel region of the diagnostic insole may be paired together.

For each pair of pressure sensors, data values corresponding to the same time may be averaged, and a histogram may be generated using the averaged values. For example, a first pressure sensor may collect 100 data values over a period of time, and a second pressure sensor paired with the first pressure sensor may collect 100 data values over the same period of time. Each of the 100 data values collected from the first pressure sensor may reflect an amount of pressure applied to the first pressure sensor at a particular point in time, and each of the 100 data values collected from the second pressure sensor may reflect an amount of pressure applied to the second pressure sensor at those same times. Each of the 100 data values collected from the first pressure sensor may be averaged with the one of the 100 data values collected from the second pressure sensor that corresponds to the second pressure sensor that corresponds to the same time, such that 100 average values are created.

A histogram may be generated using these 100 average values. A histogram corresponding to a pair of pressure sensors may allow pressure values at a location halfway between the pair of sensors to be inferred (e.g., the histogram generated using average values may be used to infer the distribution of data values that would have been collected if another pressure sensor had been placed halfway between the pair of pressure sensors whose data was averaged).

Instructions 112 may generate, based on the first and second sets of histograms, specifications for an orthosis. The specifications may include thickness and density measurements for various regions of the orthosis. In some implementations, regions of the orthosis where a person tends to put more pressure may be thinner than regions of the orthosis where the person tends to put less pressure. For example, for a person who tends to stand/walk/run on his/her heels, histograms corresponding to pressure sensors (or groups of pressure sensors) in the heel region of a diagnostic insole may have a high concentration of data values in higher value bins, and histograms corresponding to pressure sensors (or groups of pressure sensors) at the other end of the diagnostic insole (where the person's toes are) may have a high concentration of data values in lower value bins. Specifications for a custom insole may indicate that the custom insole should be thinner in the heel region than in the region under/near the toes. The amount of the difference in thickness may be determined based on how much greater data values collected from the heel region are than data values collected from the region under/near the toes (e.g., the great the difference in data values, the greater the difference in thickness).

In some implementations, regions of the orthosis where a person tends to put more pressure may be denser than regions of the orthosis where the person tends to put less pressure. For example, for a person who tends to shift weight toward the outer edges of his/her feet, histograms corresponding to pressure sensors (or groups of pressure sensors) along the outer edge of a diagnostic insole may have a high concentration of data values in higher value bins, and histograms corresponding to pressure sensors (or groups of pressure sensors) along the inner edge of the diagnostic insole may have a high concentration of data values in lower value bins. Specifications for a custom insole may indicate that the custom insole should be denser along the outer edge than along the inner edge (e.g., since the person may feel more comfortable having more cushioning/support along the outer edge, where more weight is shifted). The higher the value ranges are of the bins in which data values are concentrated, the denser an orthosis may be in the relevant region.

Figure 2:
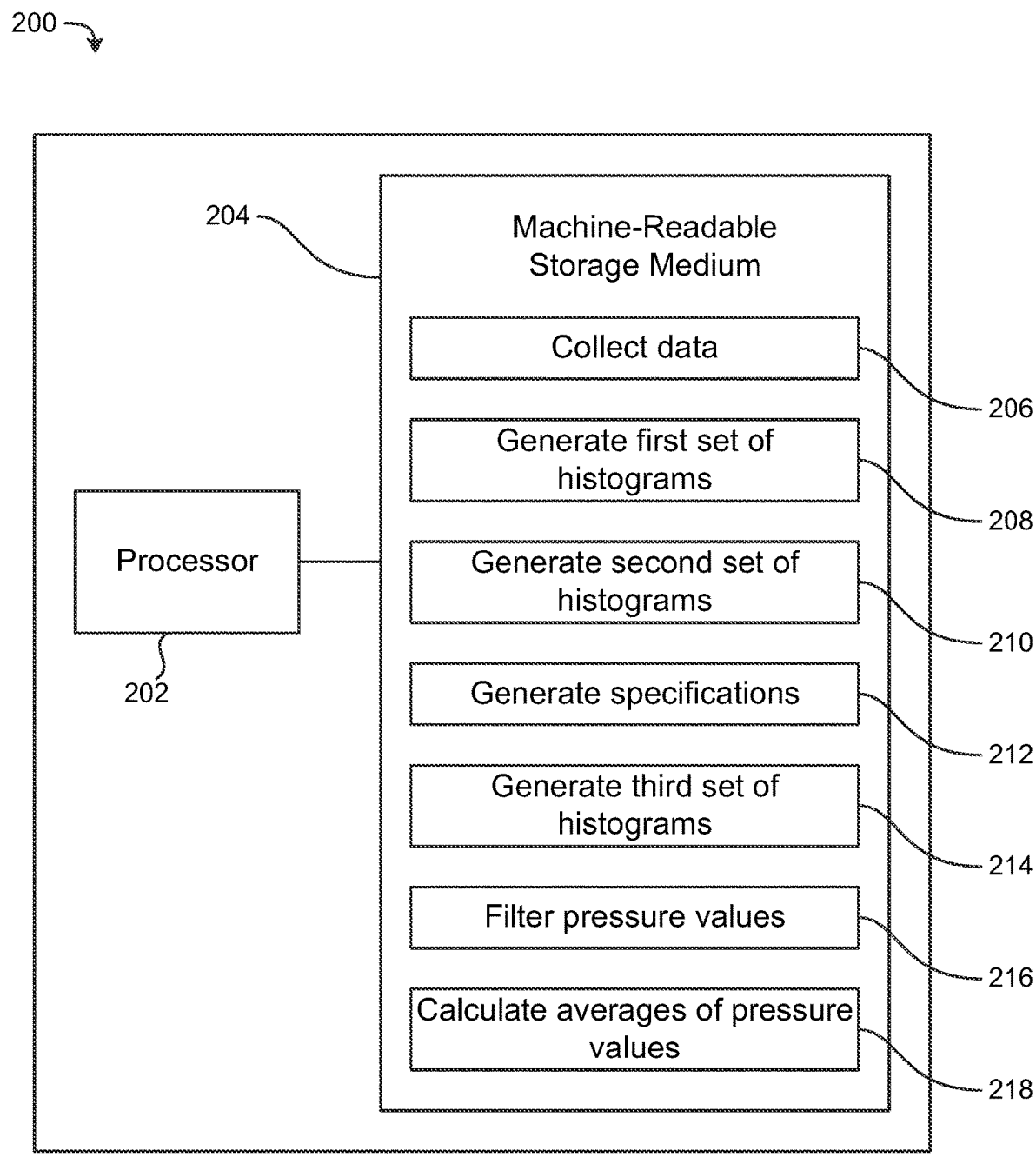
FIG. 2 is a block diagram of an example device that includes a machine-readable storage medium encoded with instructions to filter pressure values.

FIG. 2 is a block diagram of an example device 200 that includes a machine-readable storage medium encoded with instructions to filter pressure values. In some implementations, device 200 may be embedded in a diagnostic insole or other limb support structure (e.g., for a hand, shoulder, ankle, or knee). In some implementations, device 200 may be an electronic user device, such as a notebook computer, a desktop computer, a workstation, a tablet computing device, or a mobile phone. In FIG. 2, device 200 includes processor 202 and machine-readable storage medium 204.

As with processor 102 of FIG. 1, processor 202 may include a CPU, microprocessor (e.g., semiconductor-based microprocessor), and/or other hardware device suitable for retrieval and/or execution of instructions stored in machine-readable storage medium 204. Processor 202 may fetch, decode, and/or execute instructions 206, 208, 210, 212, 214, 216, and 218. As an alternative or in addition to retrieving and/or executing instructions, processor 202 may include an electronic circuit comprising a number of electronic components for performing the functionality of instructions 206, 208, 210, 212, 214, 216, and/or 218.

As with machine-readable storage medium 104 of FIG. 1, machine-readable storage medium 204 may be any suitable physical storage device that stores executable instructions. Instructions 206, 208, 210, and 212 on machine-readable storage medium 204 may be analogous to (e.g., have functions and/or components similar to) instructions 106, 108, 110, and 112, respectively, on machine-readable storage medium 104. Instructions 206 may collect data from a plurality of pressure sensors, and instructions 208 and 210 may generate a first set and a second set of histograms, respectively. Instructions 214 may generate a third set of histograms. Each histogram in the third set of histograms may correspond to a respective triplet of the plurality of pressure sensors, and may characterize a distribution of averages of data collected from the respective triplet of the plurality of pressure sensors. Pressure sensors in the plurality of pressure sensors may be grouped into triplets based on physical proximity. For example, three pressure sensors in the heel region of a diagnostic insole may be grouped together in a triplet. Three pressure sensors in or near the ball-of-the-foot region of the diagnostic insole may be grouped together in another triplet.

For each triplet of pressure sensors, data values corresponding to the same time may be averaged, and a histogram may be generated using the averaged values. For example, a first pressure sensor may collect 100 data values over a period of time, a second pressure sensor in the same triplet as the first pressure sensor may collect 100 data values over the same period of time, and a third pressure sensor in the same triplet may collect 100 data values over the same period of time. Each of the 100 data values collected from the first pressure sensor may reflect an amount of pressure applied to the first pressure sensor at a particular point in time, and each of the 100 data values collected from each of the second and third pressure sensors may reflect an amount of pressure applied to the second and third pressure sensors, respectively, at those same times. Each of the 100 data values collected from the first pressure sensor may be averaged with the one of the 100 data values collected from the second pressure sensor, and the one of the 100 data values collected from the third pressure sensor, that correspond to the same time, such that 100 average values are created. A histogram may be generated using these 100 average values. A histogram corresponding to a triplet of pressure sensors may allow pressure values at a location in the middle of the triplet of sensors to be inferred (e.g., the histogram generated using average values may be used to infer the distribution of data values that would have been collected if another pressure sensor had been placed in the middle of the triplet of pressure sensors whose data was averaged). Instructions 212 may generate specifications for an orthosis based on the first, second, and third sets of histograms. The generation of specifications based on averages of data values may allow the resulting orthosis to be better customized for more regions of a person's foot/other body part.

As discussed above with respect to FIG. 1, data collected from the plurality of pressure sensors may include pressure values. Each pressure value may indicate an amount of pressure applied to one of the plurality of pressure sensors at a certain time. Instructions 216 may filter out pressure values below a threshold value. For example, instructions 216 may filter out pressure values below 0.5 psi. Data below the threshold value may have been collected during times when a person was not putting pressure on his/her feet, for example when the person was sitting or lying down. Filtered-out pressure values may not be used to generate the first and second sets of histograms. If a third set of histograms is generated, filtered-out pressure values may not be used to generate the third set of histograms. The exclusion of filtered-out pressure values from generated histograms may allow the histograms to more accurately characterize pressure values collected when a person is on his/her feet, and thus allow more accurate specifications for an orthosis (e.g., custom insole) to be generated.

Instructions 218 may calculate, for each of the plurality of pressure sensors, an average of pressure values collected from the respective pressure sensor. For example, if a person wore a diagnostic insole for three days, an average of all pressure values collected over the three days by a particular pressure sensor on the diagnostic insole may be calculated. An average may be calculated for each pressure sensor on the diagnostic insole. In some implementations, filtered-out pressure values may not be included when calculating an average of pressure values for a pressure sensor. Specifications for an orthosis may be generated based on the calculated averages. For example, for a person who tends to stand/walk/run on his/her heels, an average of pressure values collected by a pressure sensor in the heel region of a diagnostic insole may be higher than an average of pressure values collected by a pressure sensor in the big-toe region of the diagnostic insole. Specifications for a custom insole may indicate that the custom insole should be thinner in the heel region than in the big-toe region. The amount of the difference in thickness may be determined based on how much greater the average pressure value for the pressure sensor in the heel region is than the average pressure value for the pressure sensor in the big-toe region (e.g., the great the difference in average pressure values, the greater the difference in thickness; the higher the average pressure value, the thinner the custom insole in the corresponding region).

In some implementations, specifications for an orthosis may include support values that correspond to respective thicknesses and/or densities of material. For example, support values may be assigned to various regions of an orthosis based on numerical values of averages of pressure values collected from pressure sensors in the respective regions, relative values of averages of pressure values collected from pressure sensors in the respective regions compared to averages of pressure values collected from pressure sensors in other regions, and/or where data values are concentrated in histograms corresponding to pressure sensors (or groups of pressure sensors) in the respective regions. Higher support values may correspond to lower thickness measurements and/or higher density measurements. In some implementations, a first support value for thickness and a second support value for density may be generated for each region (e.g., determined based on locations of pressure sensors in a diagnostic insole) of an orthosis.

Figure 3:
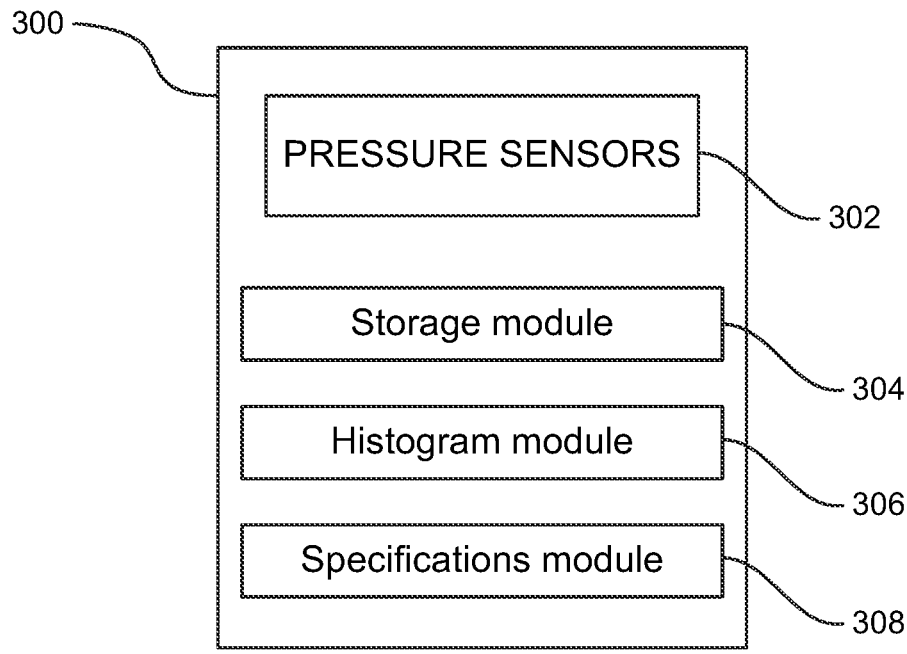
FIG. 3 is a block diagram of an example system for generating specifications for an orthosis.

FIG. 3 is a block diagram of an example system 300 for generating specifications for an orthosis. System 300 may include a plurality of pressure sensors 302, storage module 304, histogram module 306, and specifications module 308. A module may include a set of instructions encoded on a machine-readable storage medium and executable by a processor of system 300. In addition or as an alternative, a module may include a hardware device comprising electronic circuitry for implementing the functionality described below.

The plurality of pressure sensors 302 may be in various locations on a diagnostic insole or other diagnostic support structure. For example, a diagnostic insole having the plurality of pressure sensors 302 may be placed in a person's shoe, and data may be collected from the plurality of pressure sensors 302 as the person goes about his/her daily routine. Data collected from the plurality of pressure sensors 302 may include pressure values. Each pressure value may indicate an amount of pressure applied to one of the plurality of pressure sensors at a certain time.

Storage module 304 may store data collected from the plurality of pressure sensors 302. In some implementations, the stored data may include data collected from the plurality of pressure sensors 302 over a plurality of days. In some implementations, storage module 304 may be embedded in a diagnostic insole/other support structure. In some implementations, storage module 304 may be on a separate device from the diagnostic insole/other support structure. For example, storage module 304 may be on a person's smartphone. Data collected from the plurality of pressure sensors 302 may be wirelessly transmitted to the person's smartphone and stored by storage module 304.

Histogram module 306 may generate a plurality of histograms based on the stored data. In some implementations, histogram module 306 may be embedded in a diagnostic insole/other support structure. In some implementations, histogram module 306 may be on a separate device from the diagnostic insole/other support structure (e.g., on a person's smartphone or on a server to which collected/stored data is transmitted). The plurality of histograms may include a first set of histograms and a second set of histograms. Each histogram in the first set of histograms may correspond to a respective one of the plurality of pressure sensors, and may characterize a distribution of data collected from the respective one of the plurality of pressure sensors. The number of values in a bin of a histogram may be directly proportional to the amount of time the respective pressure sensor sensed an amount of pressure in the value range of the bin, as discussed above with respect to FIG. 1. Each histogram in the second set of histograms may correspond to a respective pair of the plurality of pressure sensors 302, and may characterize a distribution of averages of data collected from the respective pair of the plurality of pressure sensors 302. Pressure sensors in the plurality of pressure sensors 302 may be paired based on physical proximity, as discussed above with respect to FIG. 1.

In some implementations, the plurality of histograms may include a third set of histograms. Each histogram in the third set of histograms may correspond to a respective triplet of the plurality of pressure sensors 302, and may characterize a distribution of averages of data collected from the respective triplet of the plurality of pressure sensors 302. Pressure sensors in the plurality of pressure sensors 302 may be grouped into triplets based on physical proximity, as discussed above with respect to FIG. 2.

Specifications module 308 may generate, based on the plurality of histograms, specifications for an orthosis. In some implementations, specifications module 308 may be embedded in a diagnostic insole/other support structure. In some implementations, specifications module 308 may be on a separate device from the diagnostic insole/other support structure (e.g., on a person's smartphone or on a server to which collected/stored data is transmitted). The specifications may include thickness and density measurements for various regions of the orthosis. The regions may correspond to locations of pressure sensors in a diagnostic insole/other support structure. In some implementations, regions of the orthosis where a person tends to put more pressure may be thinner and/or denser than regions of the orthosis where the person tends to put less pressure, as discussed above with respect to FIG. 1.

Figure 4:
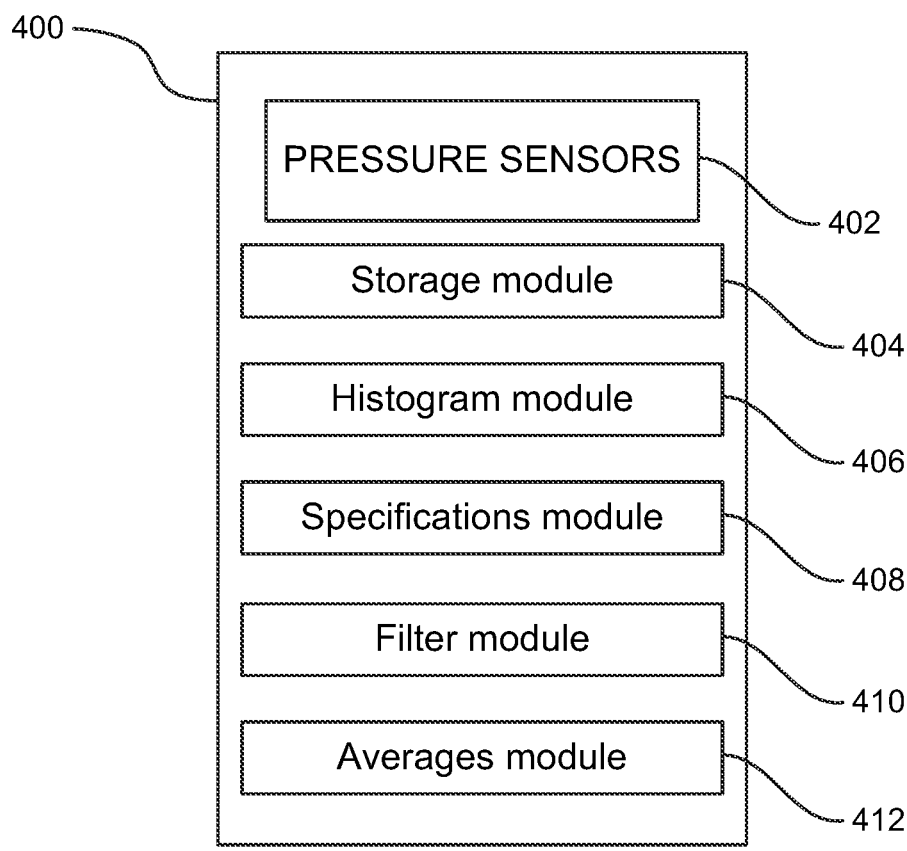
FIG. 4 is a block diagram of an example system for processing data collected by pressure sensors.

FIG. 4 is a block diagram of an example system 400 for processing data collected by pressure sensors. System 400 may include a plurality of pressure sensors 402, storage module 404, histogram module 406, specifications module 408, filter module 410, and averages module 412. A module may include a set of instructions encoded on a machine-readable storage medium and executable by a processor of system 400. In addition or as an alternative, a module may include a hardware device comprising electronic circuitry for implementing the functionality described below.

The plurality of pressure sensors 402 of system 400 may be analogous to the plurality of pressure sensors 302 of FIG. 3. Modules 404, 406, and 408 of system 400 may be analogous to modules 304, 306, and 308 of system 300. Storage module 404 may store data collected from the plurality of pressure sensors 402. The stored data may include pressure values. Each pressure value may indicate an amount of pressure applied to one of the plurality of pressure sensors at a certain time. In some implementations, the stored data may include data collected from the plurality of pressure sensors 402 over a plurality of days.

Filter module 410 may filter out pressure values below a threshold value. In some implementations, filter module 410 may be embedded in a diagnostic insole/other support structure. In some implementations, filter module 410 may be on a separate device from the diagnostic insole/other support structure (e.g., on a person's smartphone or on a server to which collected/stored data is transmitted). Data below the threshold value may have been collected during times when a person was not putting pressure on his/her feet, for example when the person was sitting or lying down. Filtered-out pressure values may not be used to generate the plurality of histograms. The exclusion of filtered-out pressure values from generated histograms may allow the histograms to more accurately characterize pressure values collected when a person is on his/her feet, and thus allow more accurate specifications for an orthosis (e.g., custom insole) to be generated.

Averages module 412 may calculate, for each of the plurality of pressure sensors 402, an average of pressure values collected from the respective pressure sensor. For example, if a person wore a diagnostic insole for two days, an average of all pressure values collected over the two days by a particular pressure sensor on the diagnostic insole may be calculated. An average may be calculated for each pressure sensor on the diagnostic insole. In some implementations, filtered-out pressure values may not be included when calculating an average of pressure values for a pressure sensor. In some implementations, averages module 412 may be embedded in a diagnostic insole/other support structure. In some implementations, averages module 412 may be on a separate device from the diagnostic insole/other support structure (e.g., on a person's smartphone or on a server to which collected/stored data is transmitted). Specifications module 408 may generate specifications for an orthosis based on the calculated averages, as discussed above with respect to FIG. 2. In some implementations, specifications for an orthosis may include support values that correspond to respective thicknesses and/or densities of material, as discussed above with respect to FIG. 2.

Figure 5:
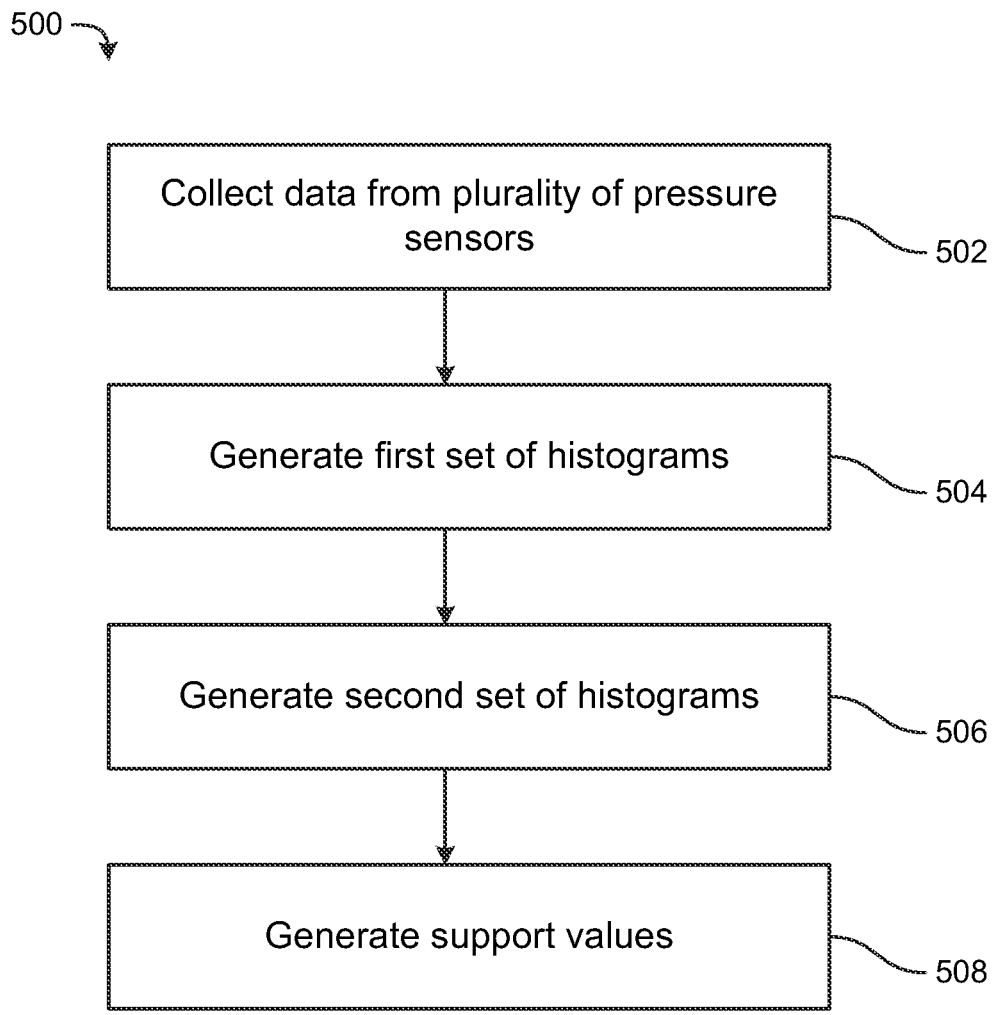
FIG. 5 is a flowchart of an example method for generating support values for an orthosis.
Figure 6:
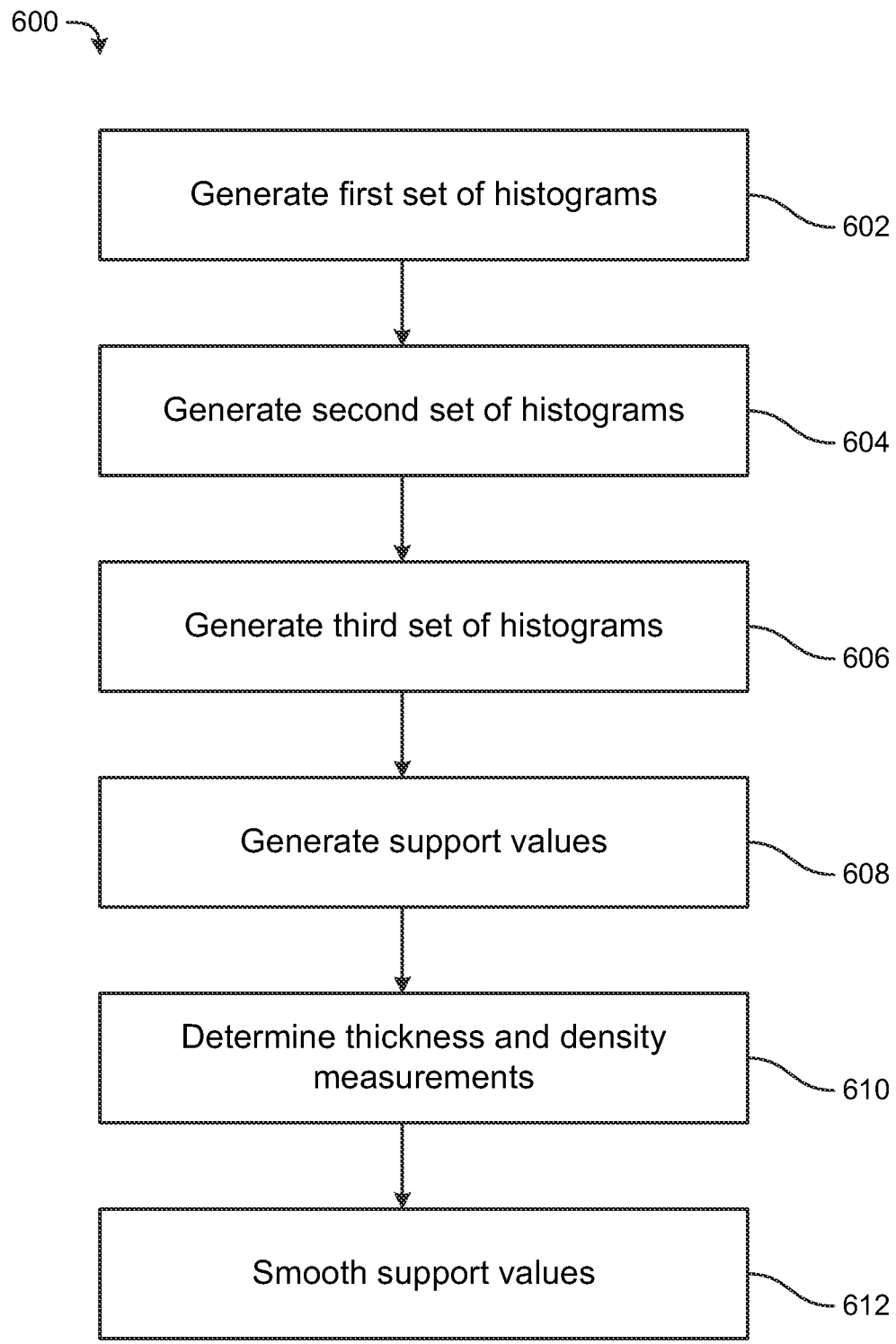
FIG. 6 is a flowchart of an example method for generating a model for a three-dimensional (3D) printer to print an orthosis.
Figure 7:
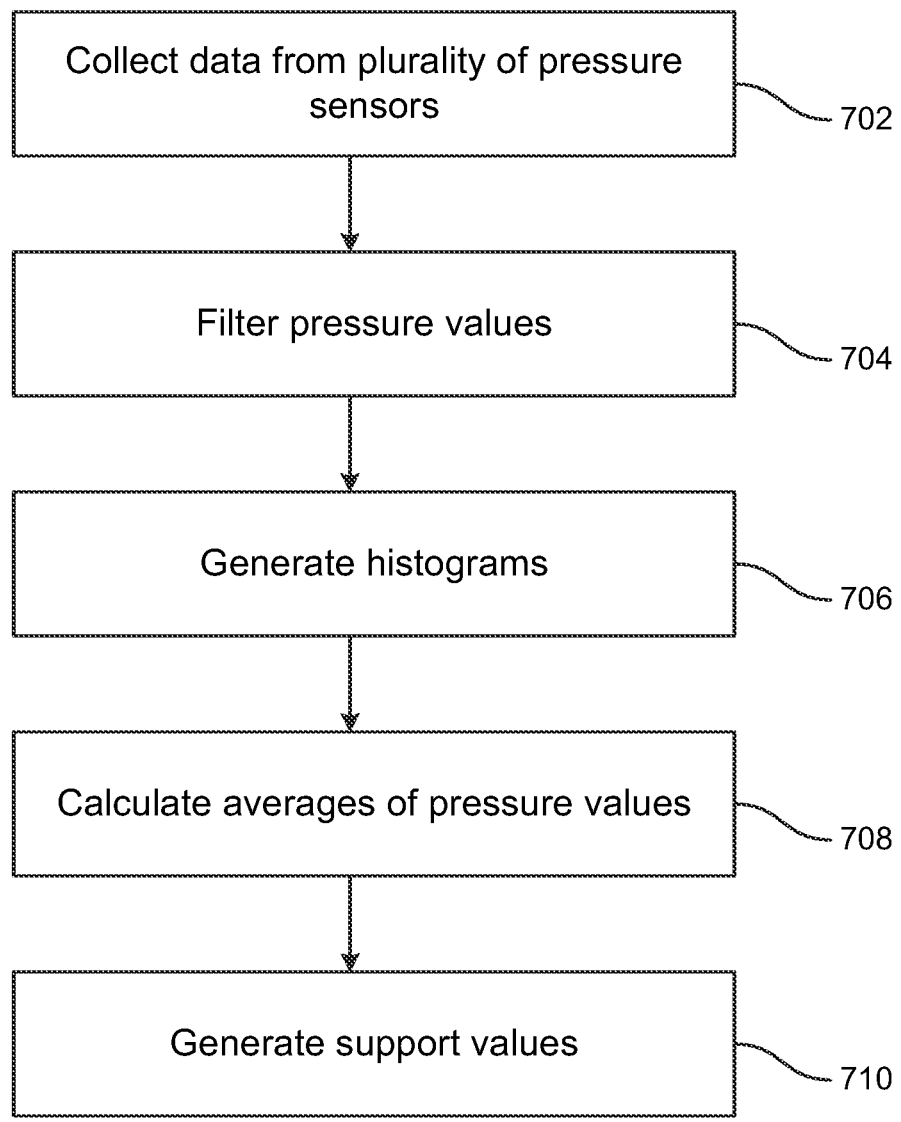
FIG. 7 is a flowchart of an example method for processing data collected by pressure sensors.

Methods related to collecting data from pressure sensors for purposes of creating a custom orthosis are discussed with respect to FIGS. 5-7. FIG. 5 is a flowchart of an example method 500 for generating support values for an orthosis. Although execution of method 500 is described below with reference to processor 102 of FIG. 1, it should be understood that execution of method 500 may be performed by other suitable devices, such as processor 202 of FIG. 2. Method 500 may be implemented in the form of executable instructions stored on a machine-readable storage medium and/or in the form of electronic circuitry.

Method 500 may start in block 502, where processor 102 may collect, over a plurality of days, data from a plurality of pressure sensors. The plurality of pressure sensors may be in various locations on a diagnostic insole. For example, a diagnostic insole having the plurality of pressure sensors may be placed in a person's shoe, and data may be collected from the plurality of pressure sensors as the person goes about his/her daily routine during the plurality of days. Data collected from the plurality of pressure sensors may include pressure values. Each pressure value may indicate an amount of pressure applied to one of the plurality of pressure sensors at a certain time.

In block 504, processor 102 may generate a first set of histograms. Each histogram in the first set of histograms may correspond to a respective one of the plurality of pressure sensors, and may characterize a distribution of data collected from the respective one of the plurality of pressure sensors. The number of values in a bin of a histogram may be directly proportional to the amount of time the respective pressure sensor sensed an amount of pressure in the value range of the bin, as discussed above with respect to FIG. 1.

In block 506, processor 102 may generate a second set of histograms. Each histogram in the second set of histograms may correspond to a respective pair of the plurality of pressure sensors, and may characterize a distribution of averages of data collected from the respective pair of the plurality of pressure sensors. Pressure sensors in the plurality of pressure sensors may be paired based on physical proximity, as discussed above with respect to FIG. 1. Although block 506 is shown below block 504 in FIG. 5, it should be understood that elements of block 506 may be performed before or in parallel with elements of block 504.

In block 506, processor 102 may generate, based on the first and second sets of histograms, support values for an orthosis. A support value may correspond to a particular thickness and/or density of material. In some implementations, support values may be assigned to various regions of an orthosis based on numerical values of averages of pressure values collected from pressure sensors in the respective regions, relative values of averages of pressure values collected from pressure sensors in the respective regions compared to averages of pressure values collected from pressure sensors in other regions, and/or where data values are concentrated in histograms, of the first and second sets of histograms, corresponding to pressure sensors (or groups of pressure sensors) in the respective regions. Higher support values may correspond to lower thickness measurements and/or higher density measurements. In some implementations, a first support value for thickness and a second support value for density may be generated for each region (e.g., determined based on locations of pressure sensors in a diagnostic insole) of an orthosis.

FIG. 6 is a flowchart of an example method 600 for generating a model for a three-dimensional (3D) printer to print an orthosis. Although execution of method 600 is described below with reference to processor 202 of FIG. 2, it should be understood that execution of method 600 may be performed by other suitable devices, such as processor 102 of FIG. 1. Some blocks of method 600 may be performed in parallel with and/or after method 500. Method 600 may be implemented in the form of executable instructions stored on a machine-readable storage medium and/or in the form of electronic circuitry.

Method 600 may start in block 602, where processor 202 may generate a first set of histograms. In block 604, processor 202 may generate a second set of histograms. Blocks 602 and 604 of FIG. 6 may be analogous to blocks 504 and 506, respectively of FIG. 5. Although block 604 is shown below block 602 in FIG. 6, it should be understood that elements of block 604 may be performed before or in parallel with elements of block 602.

In block 606, processor 202 may generate a third set of histograms. Each histogram in the third set of histograms may correspond to a respective triplet of a plurality of pressure sensors, and may characterize a distribution of averages of data collected from the respective triplet of the plurality of pressure sensors. Pressure sensors in the plurality of pressure sensors may be grouped into triplets based on physical proximity, as discussed above with respect to FIG. 2.

In block 608, processor 202 may generate support values for an orthosis based on the first, second, and third sets of histograms. In some implementations, support values may be assigned to various regions of an orthosis based on where data values are concentrated in histograms, of the first, second, and third sets of histograms, corresponding to pressure sensors (or groups of pressure sensors) in the respective regions. For example, if a histogram corresponding to a first pressure sensor has a high concentration of data values in high-value bins, a high support value may be generated for a region of an orthosis corresponding to the location of the first pressure sensor. If a histogram corresponding to a second pressure sensor has a high concentration of data values in low-value bins, a low support value may be generated for a region of the orthosis corresponding to the location of the second pressure sensor. In some implementations, a first support value for thickness and a second support value for density may be generated for each region (e.g., determined based on locations of pressure sensors in a diagnostic insole) of an orthosis.

In block 610, processor 202 may determine, based on the support values, thickness and density measurements for various regions of the orthosis. A support value may correspond to a particular thickness and/or density of material. Higher support values may correspond to lower thickness measurements and/or higher density measurements.

In block 612, processor 202 may smooth support values to generate a model for the orthosis. For example, fifteen support values may be generated, each corresponding to a respective region of the orthosis and to a respective thickness and/or density for the respective region. Processor 202 may apply a smoothing function, such as a moving average function, to the fifteen support values to allow a more gradual transition in thickness and/or density between different regions. The generated model may be used by a 3D printer to print the orthosis. Thus, a 3D printer may be used to print the orthosis without scanning a person's foot or a cast/mold of the person's foot.

FIG. 7 is a flowchart of an example method 700 for processing data collected by pressure sensors. Although execution of method 700 is described below with reference to processor 202 of FIG. 2, it should be understood that execution of method 700 may be performed by other suitable devices, such as processor 102 of FIG. 1. Some blocks of method 700 may be performed in parallel with and/or after method 500 and/or 600. Method 700 may be implemented in the form of executable instructions stored on a machine-readable storage medium and/or in the form of electronic circuitry.

Method 700 may start in block 702, where processor 202 may collect data from a plurality of pressure sensors. The plurality of pressure sensors may be in various locations on a diagnostic insole. For example, a diagnostic insole having the plurality of pressure sensors may be placed in a person's shoe, and data may be collected from the plurality of pressure sensors as the person goes about his/her daily routine. Data collected from the plurality of pressure sensors may include pressure values. Each pressure value may indicate an amount of pressure applied to one of the plurality of pressure sensors at a certain time. In some implementations, data may be collected from the plurality of pressure sensors over a plurality of days.

In block 704, processor 202 may filter out pressure values below a threshold value. For example, processor 202 may filter out pressure values below 0.3 psi. Data below the threshold value may have been collected during times when a person was not putting pressure on his/her feet, for example when the person was sitting or lying down.

In block 706, processor 202 may generate a plurality of histograms. The plurality of histograms may include a first set of histograms that characterize a distribution of data collected from respective ones of the plurality of pressure sensors, and a second set of histograms that characterize a distribution of averages of data collected from respective pairs of the plurality of pressure sensors, as discussed above with respect to FIG. 1. Filtered-out pressure values may not be used to generate the first and second sets of histograms. In some implementations, the plurality of histograms may include a third set of histograms that characterize a distribution of averages of data collected from respective triplets of the plurality of pressure sensors, as discussed above with respect to FIG. 2. Filtered-out pressure values may not be used to generate the third set of histograms. The exclusion of filtered-out pressure values from generated histograms may allow the histograms to more accurately characterize pressure values collected when a person is on his/her feet, and thus allow more accurate specifications for an orthosis (e.g., custom insole) to be generated.

In block 708, processor 202 may calculate, for each of the plurality of pressure sensors, an average of pressure values collected from the respective pressure sensor. For example, if a person wore a diagnostic insole for three days, processor 202 may calculate an average of all pressure values collected over the three days by a particular pressure sensor on the diagnostic insole. Processor 202 may calculate an average for each pressure sensor on the diagnostic insole. In some implementations, filtered-out pressure values may not be included when calculating an average of pressure values for a pressure sensor.

In block 710, processor 202 may generate support values based on the plurality of histograms and the calculated averages. In some implementations, support values may be assigned to various regions of an orthosis based on numerical values of averages of pressure values collected from pressure sensors in the respective regions, relative values of averages of pressure values collected from pressure sensors in the respective regions compared to averages of pressure values collected from pressure sensors in other regions, and/or where data values are concentrated in histograms corresponding to pressure sensors (or groups of pressure sensors) in the respective regions. Support values may correspond to respective thicknesses and/or densities of material, as discussed above with respect to FIG. 2. In some implementations, a first support value for thickness and a second support value for density may be generated for each region (e.g., determined based on locations of pressure sensors in a diagnostic insole) of an orthosis.

The foregoing disclosure describes using a diagnostic insole/other support structure having a plurality of pressure sensors to collect data as a person goes about his/her daily activities. Example implementations described herein enable the creation of a custom orthosis suited to actual conditions in a person's daily life.

I claim:

1. A non-transitory machine-readable medium containing computer instructions stored therein for causing a computer processor to perform:
   collecting, over a plurality of activities, pressure data from a plurality of pressure sensors of a diagnostic insole, wherein the plurality of pressure sensors of the diagnostic insole includes at least three pressure sensors;
   generating a first set of histograms, wherein each histogram in the first set of histograms:
      corresponds to a respective one of the plurality of pressure sensors, and
      characterizes a distribution of pressure data collected from the respective one of the plurality of pressure sensors;
   generating a second set of histograms, wherein each histogram in the second set of histograms:
      corresponds to a respective pair of the plurality of pressure sensors, and
      characterizes a distribution of averages of pressure data collected from the respective pair of the plurality of pressure sensors;
   generating a third set of histograms, wherein each histogram in the third set of histograms:
      corresponds to a respective triplet of the plurality of pressure sensors;
      characterizes a distribution of averages of pressure data collected from the respective triplet of the plurality of pressure sensors; and
   generating, based on the first, the second, and the third sets of histograms, specifications for an orthosis, wherein the specifications include support values corresponding to various regions of the orthosis.

2. The non-transitory machine-readable medium of claim 1, wherein the pressure data from the plurality of pressure sensors comprises pressure values, wherein each pressure value indicates an amount of pressure applied to each of the plurality of pressure sensors at a certain time, and the instructions cause the computer processor to further perform:
   filtering out pressure values below a threshold value, wherein the filtered-out pressure values are not used to generate the first, the second, and the third sets of histograms.

3. The non-transitory machine-readable medium of claim 1, wherein the pressure data from the plurality of pressure sensors is collected over a plurality of days.

4. The non-transitory machine-readable medium of claim 1, wherein the pressure data from the plurality of pressure sensors comprises pressure values, wherein each pressure value indicates an amount of pressure applied to one of the plurality of pressure sensors at a certain time, and the instructions cause the computer processor to further perform:

calculating, for each of the plurality of pressure sensors, an average of pressure values collected from each respective pressure sensor; and
generating the support values based on the calculated average.

5. The non-transitory machine-readable medium of claim 1, wherein the support values indicate thickness and density measurements for the various regions of the orthosis.

6. The non-transitory machine-readable medium of claim 1, wherein each histogram in the first set of histograms comprises a plurality of bins, wherein each bin of the plurality of bins includes pressure values from the respective one of the plurality of pressure sensors.

7. The non-transitory machine-readable medium of claim 6, wherein each bin of the plurality of bins corresponds to a range of pressure values corresponding to the respective one of the plurality of pressure sensors.

8. The non-transitory machine-readable medium of claim 7, wherein the range of pressure values has a width of 1.5 pounds per square inch (psi).

9. The non-transitory machine-readable medium of claim 1, wherein each histogram in the second set of histograms comprises a plurality of bins, wherein each bin of the plurality of bins includes average pressure values from the respective pair of the plurality of pressure sensors.

10. The non-transitory machine-readable medium of claim 9, wherein each bin of the plurality of bins corresponds to a range of average pressure values corresponding to the respective pair of the plurality of pressure sensors.

11. The non-transitory machine-readable medium of claim 9, wherein the range of average pressure values has a width of 1.5 pounds per square inch (psi).

12. The non-transitory machine-readable medium of claim 1, wherein each histogram in the third set of histograms comprises a plurality of bins, wherein each bin of the plurality of bins includes average pressure values from the respective triplet of the plurality of pressure sensors.

13. The non-transitory machine-readable medium of claim 12, wherein each bin of the plurality of bins corresponds to a range of average pressure values corresponding to the respective triplet of the plurality of pressure sensors.

14. A system comprising:
at least one processor;
a memory storing instructions that, when executed by the at least one processor, cause the system to perform:
collecting, over a plurality of activities, pressure data from a plurality of pressure sensors of a diagnostic insole, wherein the plurality of pressure sensors of the diagnostic insole includes at least three pressure sensors;
generating, a first set of histograms, wherein each histogram in the first set of histograms:
corresponds to a respective one of the plurality of pressure sensors, and
characterizes a distribution of pressure data collected from the respective one of the plurality of pressure sensors; and
generating, a second set of histograms, wherein each histogram in the second set of histograms:
corresponds to a respective pair of the plurality of pressure sensors, and
characterizes a distribution of averages of pressure data collected from the respective pair of the plurality of pressure sensors;
generating a third set of histograms, wherein each histogram in the third set of histograms:
corresponds to a respective triplet of the plurality of pressure sensors;
characterizes a distribution of averages of pressure data collected from the respective triplet of the plurality of pressure sensors; and
generating, based on the first, the second, and the third sets of histograms, specifications for an orthosis, wherein the specifications include support values corresponding to various regions of the orthosis.

15. The system of claim 14, wherein the pressure data from the plurality of pressure sensors comprises pressure values, wherein each pressure value indicates an amount of pressure applied to each of the plurality of pressure sensors at a certain time, and wherein the instructions cause the system to further perform:
filtering out pressure values below a threshold value, wherein the filtered-out pressure values are not used to generate the first, the second, and the third sets of histograms;
calculating, for each of the plurality of pressure sensors, an average of pressure values collected from each respective pressure sensor; and
generating the support values based on the calculated average.

16. The system of claim 14, wherein the pressure data from the plurality of pressure sensors comprises data collected over a plurality of days.

17. A method comprising:
collecting, over a plurality of activities, pressure data from a plurality of pressure sensors of a diagnostic insole, wherein the plurality of pressure sensors of the diagnostic insole includes at least three pressure sensors;
generating a first set of histograms, wherein each histogram in the first set of histograms:
corresponds to a respective one of the plurality of pressure sensors, and
characterizes a distribution of pressure data collected from the respective one of the plurality of pressure sensors;
generating a second set of histograms, wherein each histogram in the second set of histograms:
corresponds to a respective pair of the plurality of pressure sensors, and
characterizes a distribution of averages of pressure data collected from the respective pair of the plurality of pressure sensors;
generating a third set of histograms, wherein each histogram in the third set of histograms:
corresponds to a respective triplet of the plurality of pressure sensors;
characterizes a distribution of averages of pressure data collected from the respective triplet of the plurality of pressure sensors; and
generating, based on the first, the second, and the third sets of histograms, specifications for an orthosis, wherein the specifications include support values corresponding to various regions of the orthosis.

18. The method of claim 17, further comprising:
determining, based on the support values, thickness and density measurements for the various regions of the orthosis.

19. The method of claim 17, further comprising:
smoothing the support values to generate a model for the orthosis, wherein the generated model is used by a three-dimensional (3D) printer to print the orthosis.

20. The method of claim 17, wherein the pressure data from the plurality of pressure sensors comprises pressure values, wherein each pressure value indicates an amount of pressure applied to each of the plurality of pressure sensors at a certain time, and the method further comprising:
- filtering out pressure values below a threshold value, wherein the filtered-out pressure values are not used to generate the first, the second, and the third sets of histograms;
- calculating, for each of the plurality of pressure sensors, an average of pressure values collected from the respective pressure sensor; and
- generating the support values based on the calculated average.

\* \* \* \* \*